US010249025B2

(12) United States Patent
Reinhardt

(10) Patent No.: US 10,249,025 B2
(45) Date of Patent: Apr. 2, 2019

(54) ATMOSPHERIC CHANNEL CHARACTERIZATION SYSTEM AND METHOD USING TARGET IMAGE INFORMATION

(71) Applicant: THE UNITED STATES OF AMERICA AS REPRESENTED BY THE SECRETARY OF THE NAVY, Washington, DC (US)

(72) Inventor: Colin N. Reinhardt, Seattle, WA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 337 days.

(21) Appl. No.: 15/058,505

(22) Filed: Mar. 2, 2016

(65) Prior Publication Data
US 2017/0011499 A1    Jan. 12, 2017

Related U.S. Application Data

(60) Provisional application No. 62/189,082, filed on Jul. 6, 2015, provisional application No. 62/189,041, filed on Jul. 6, 2015.

(51) Int. Cl.
*G06K 9/00*    (2006.01)
*G06T 5/00*    (2006.01)
(Continued)

(52) U.S. Cl.
CPC ......... *G06T 5/001* (2013.01); *G01N 15/0205* (2013.01); *G01N 21/53* (2013.01);
(Continued)

(58) Field of Classification Search
CPC ....... G06T 5/001; G01S 17/107; G01S 7/497; G01S 7/4816; G01S 7/4815; G01S 17/95;
(Continued)

(56) References Cited

U.S. PATENT DOCUMENTS 7,379,164 B2    5/2008    Inbar et al.
8,269,950 B2    9/2012    Spinelli et al.
(Continued)

OTHER PUBLICATIONS

Colin N. Reinhardt, D.Wayne, K. McBryde, G. Cauble; Extracting Atmospheric Turbulence and Aerosol Characteristics from Passive Imagery; Proc. SPIE 8874, Laser Communication and Propagation through the Atmosphere and Oceans II, 88740F, Sep. 25, 2013.
(Continued)

*Primary Examiner* — Andrew M Moyer
(74) *Attorney, Agent, or Firm* — SPAWAR Systems Center Pacific; Kyle Eppele; Ryan J. Friedl

(57) ABSTRACT

A system and method involve transmitting, using an optical device, a plurality of optical pulses into an atmospheric propagation channel towards a target object. Using an imaging device, more than one optical signals and an image of the target object are detected from the atmospheric propagation channel. The optical signals are produced by interaction between the transmitted optical pulses and the atmospheric propagation channel and include elastic backscatter return signals, inelastic backscatter return signals, and polarization signals. A processor simultaneously processes the elastic and inelastic backscatter return signals, the polarization signals, and information contained within the image of the target to determine estimates of one or more physical parameters of the atmospheric propagation channel. The processor uses machine learning algorithms to enhance/restore the image of the target, to perform pattern-recognition and classification of the target, and to extract additional atmospheric propagation channel physical characteristics.

2 Claims, 6 Drawing Sheets

(51) Int. Cl.
*G01N 21/53* (2006.01)
*G01N 15/02* (2006.01)
*G01S 17/10* (2006.01)
*G01S 17/89* (2006.01)
*G01S 17/95* (2006.01)
*G01S 7/481* (2006.01)
*G01S 7/497* (2006.01)
*G01N 21/65* (2006.01)
*G01N 21/17* (2006.01)
*G01N 21/47* (2006.01)
*G01N 15/00* (2006.01)
*G01S 7/499* (2006.01)

(52) U.S. Cl.
CPC .......... *G01S 7/4815* (2013.01); *G01S 7/4816* (2013.01); *G01S 7/497* (2013.01); *G01S 17/107* (2013.01); *G01S 17/89* (2013.01); *G01S 17/95* (2013.01); *G01N 21/65* (2013.01); *G01N 2015/0026* (2013.01); *G01N 2015/0046* (2013.01); *G01N 2021/1793* (2013.01); *G01N 2021/4709* (2013.01); *G01N 2201/0697* (2013.01); *G01S 7/499* (2013.01); *G06T 2207/20081* (2013.01); *G06T 2207/20084* (2013.01)

(58) Field of Classification Search
CPC ..... G01S 17/89; G01S 7/499; G01N 15/0205; G01N 21/53; G01N 2015/0026; G01N 2015/0046; G01N 2201/0697; G01N 2021/4709
USPC .......................................................... 382/274
See application file for complete search history.

(56) References Cited

U.S. PATENT DOCUMENTS 9,129,369 B1 9/2015 Wayne et al.
2010/0280765 A1* 11/2010 Marquardt ............ G01N 21/21
  702/24
2018/0045571 A1* 2/2018 Shiozawa .............. G01N 21/65

OTHER PUBLICATIONS

Ishimaru, A., "Wave Propagation and Scattering in Random Media", Proceedings of the IEEE, vol. 65, No. 7, pp. 1030-1059, 1977.

* cited by examiner

ATMOSPHERIC CHANNEL CHARACTERIZATION SYSTEM AND METHOD USING TARGET IMAGE INFORMATION

CROSS-REFERENCE TO RELATED APPLICATIONS

This application claims the benefit of U.S. Provisional Patent Application Ser. No. 62/189,082 filed Jul. 6, 2015, entitled "Range-Gated Intensified CCD Imager for Single-Ended Atmospheric Characterization", and U.S. Provisional Patent Application Ser. No. 62/189,041 filed Jul. 6, 2015, entitled "Machine Learning Method for the Analysis of Turbulence- and Extinction-Degraded Imagery", the content of both of which being fully incorporated by reference herein.

FEDERALLY SPONSORED RESEARCH AND DEVELOPMENT

This invention is assigned to the United States Government. Licensing inquiries may be directed to Office of Research and Technical Applications, Space and Naval Warfare Systems Center, Pacific, Code 72120, San Diego, Calif., 92152; telephone (619) 553-5118; email: ssc_pac_t2@navy.mil. Reference Navy Case No. 103398.

BACKGROUND OF THE INVENTION

The capability to rapidly and accurately spatially and temporally characterize atmospheric conditions affecting the performance of electro-optical systems such as directed-energy systems, imaging systems, and communications links remains an inadequately solved problem. Improved systems and methods that can help achieve this capability are highly desirable.

DETAILED DESCRIPTION OF SOME EMBODIMENTS

Reference in the specification to "one embodiment" or to "an embodiment" means that a particular element, feature, structure, or characteristic described in connection with the embodiments is included in at least one embodiment. The appearances of the phrases "in one embodiment", "in some embodiments", and "in other embodiments" in various places in the specification are not necessarily all referring to the same embodiment or the same set of embodiments.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or.

Additionally, use of the "a" or "an" are employed to describe elements and components of the embodiments herein. This is done merely for convenience and to give a general sense of the invention. This detailed description should be read to include one or at least one and the singular also includes the plural unless it is obviously meant otherwise.

Figure 1:
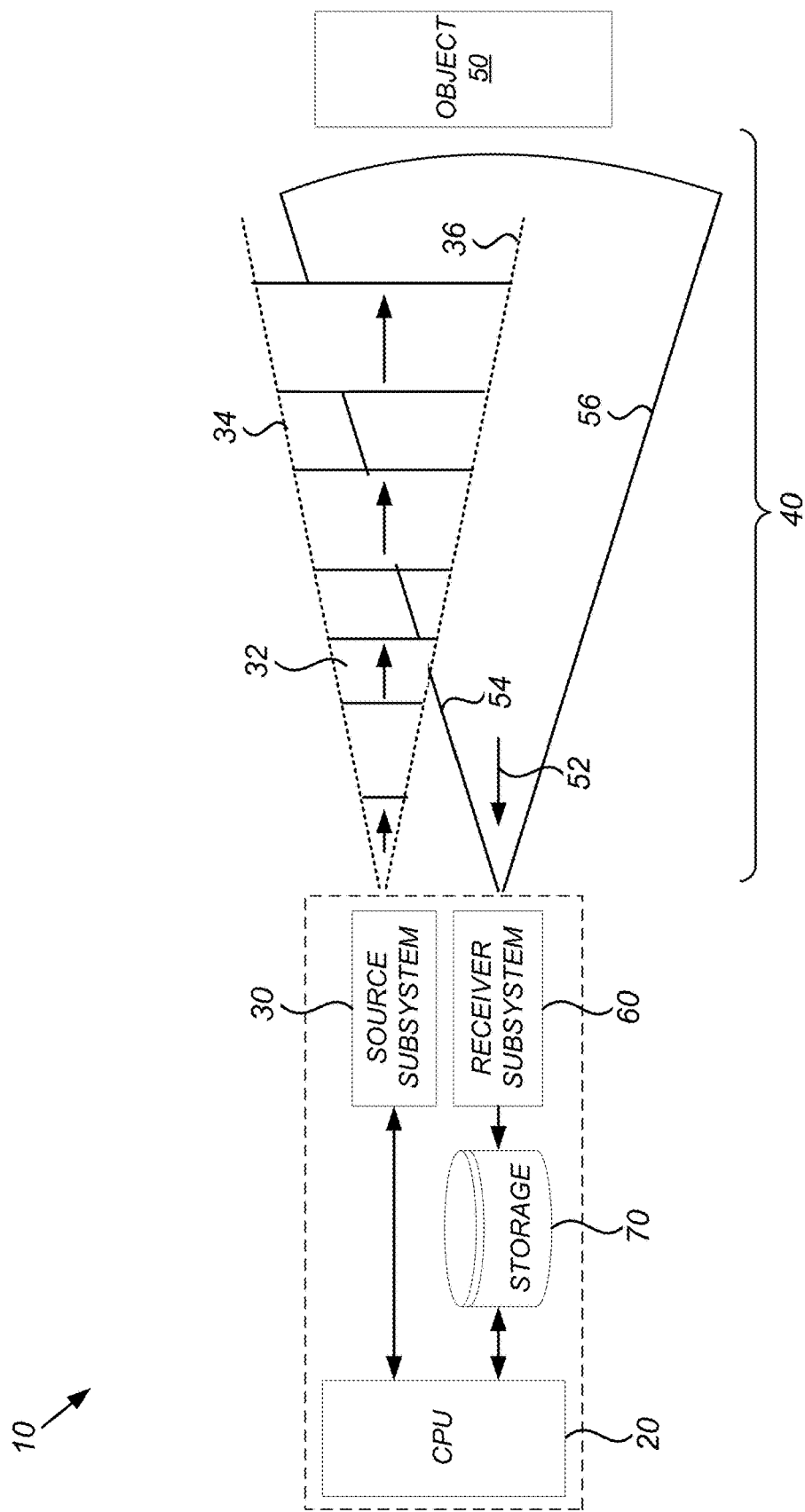
FIG. 1 shows a high level block diagram of an embodiment of a system in accordance with the Atmospheric Channel Characterization System and Method Using Target Image Information.

FIG. 1 shows a high level block diagram of an embodiment of a system 10 in accordance with the Atmospheric Channel Characterization System and Method Using Target Image Information. System 10 includes a CPU 20 operatively connected to a source subsystem 30, a receiver subsystem 60, and a storage device 70. As used herein, CPU 20 includes any type of processor or processing unit or architecture, such as a graphics processing unit (GPU), accelerated processing unit (APU), core processor, or any other type of processing device regardless of the number of processing cores therein. CPU 20 may also be referred to herein as a "processor", GPU, APU, etc.

Source subsystem 30, which may be an optical-based subsystem, is configured to transmit a plurality of optical pulses 32, such as hyperspectral optical pulses, into an atmospheric propagation channel 40. As an example, pulses 32 may have a profile defined by lines 34 and 36 shown n FIG. 1. Further, as an example, the plurality of optical pulses may be comprised of various combinations of one or more of different wavelengths, different pulse durations/energy-levels, different polarizations (e.g. linear and/or circular), different coherence profiles, and different beam spatial profiles (e.g. Gaussian, Bessel, Gauss-Laguerre, flat-top).

Atmospheric propagation channel 40 may include characteristics of interest for retrieval including, for example, 3D range-resolved profiles of: visibility, optical depth, wind velocity, air temperature, relative humidity, water vapor content, atmospheric turbulent intensity levels, inner & outer scale of turbulence, aerosol and particulate size and chemical compositions, aerosol size distribution functions, cloud and fog microphysical information, Angstrom coefficient.

In some embodiments, the optical pulses are directed towards a target 50. In some embodiments, the target is an arbitrary target of opportunity within an observed environment. For example, in a maritime environment target 50 could be a stationary or transitory vessel, in a land-based environment target 50 could be a structure, and in an air-based environment target 50 could be an aircraft. Further, in some embodiments, target 50 need not be a "man-made" object, but could be, for example, the sea surface itself, a cloud, or forest canopy. Such targets 50 may be useful in applications such as remote sensing for meteorology, atmospheric sciences, and environmental monitoring.

Figure 2:
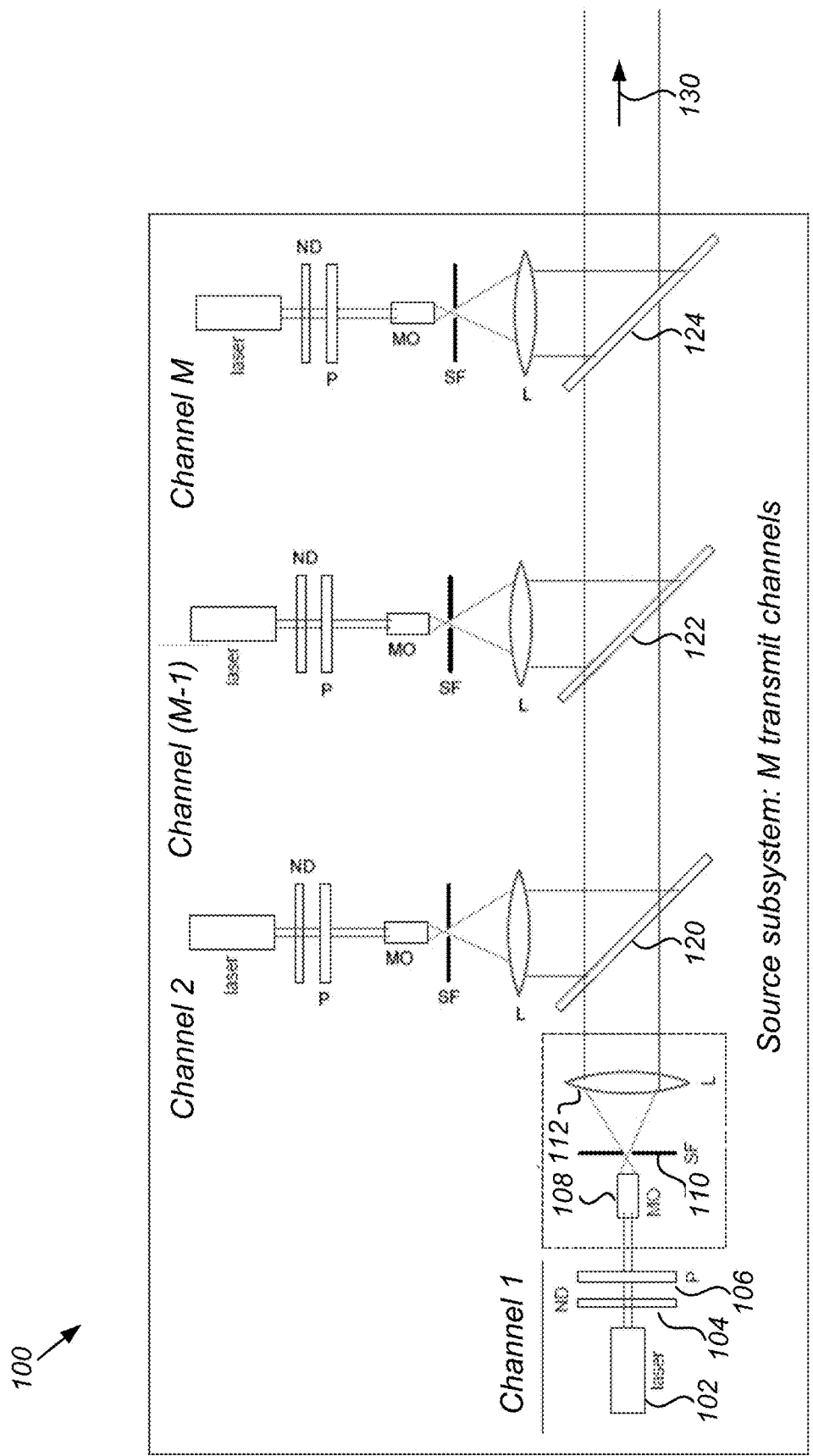
FIG. 2 shows a block diagram of an embodiment of a source sub-system in accordance with the Atmospheric Channel Characterization System and Method Using Target Image Information.

FIG. 2 shows a block diagram of an embodiment of a source subsystem 100 that may be used, for example, within system 10 and may serve as source subsystem 30. As shown, system 100 includes a plurality of optical channels 1-M. As an example, each of the channels may be tuned to a separate wavelength. Each channel may further include optical components configured to combine the output of the optical channels to produce the plurality of optical pulses. As an example, each channel may include an optical source 102 which outputs an optical signal towards a non-dichromatic filter 104.

In some embodiments, optical source 102 is a multispectral source that is configured for high-speed short-duration pulses. As an example, optical source 102 may comprise a Nd:YAG (1060/532/355)+Ti:Sap (800/400 nm) laser with a pulse duration of about 1 ns and having a pulse energy of between about 10 mJ and 100 mJ. The filtered signal may then encounter a polarizing filter 106, a microscope objective lens 108, a spatial filter 110, and then a collimating lens 112. Further, each channel may be configured to output an optical pulse having any of the variable properties described above.

An array of aligned optical combiners is positioned adjacent to the collimating lenses from the channels. The output of channels 1 and 2 are combined by a lens 120, which is then combined with the output of channel (M-1) by lens 122, with the output of channel (M-1) being combined with the output of channel M by lens 124 and directed in the direction of arrow 130 to the environment via the atmospheric propagation channel. In some embodiments, prior to transmission to the atmospheric propagation channel, the combined optical signal may encounter additional components that may include one or more elements to control beam spatial profiles, coherence, pulse duration and/or optical power/energy, and polarization of the transmitted optical signal.

In some embodiments, it may be desirable to use a timing synchronization unit (not shown in system 100) to transmit each output channel in a repeating sequence, where each channel is enabled in turn for a specified duration $t_m$, with a interleaved delay interval of $t_{delay\_m}$, and the entire sequence repeats every $t_m$. This synchronization device would then also control the receiver subsystem 60, to synchronize the appropriate individual receive channel(s) with the corresponding transmitted output channel(s).

In some embodiments, it may be desirable to use a more elaborate beam-combiner design, such that the output channels may be directed to more than one output aperture, either to provide spatial diversity, or to allow different aperture parameters and optical designs for each output aperture.

Receiver subsystem 60, which may be an optical-based subsystem, is configured to receive signals, represented by arrow 52 in FIG. 1, from atmospheric propagation channel 40 and from the remote target 50. Signals 52 are produced by interaction between transmitted optical pulses 32 and atmospheric propagation channel 40 or the remote target 50. Signals 52 may be received from a field of view (FOV) defined, for example, by lines 54 and 56 shown in FIG. 1. As an example, signals 52 may comprise any one of or a combination of the following: elastic and inelastic backscatter from aerosols, particles, and/or other particulates located within the atmospheric propagation channel, reflected signals off of a target, such as target 50, reflected signals off background clutter objects, and polarization signals.

Receiving subsystem 60 may comprise an optical receiver subsystem having an imaging device configured to detect optical signals from the atmospheric propagation channel. In some embodiments, the imaging device may have a variable FOV capability, so that signals may be acquired using multiple FOVs. The optical signals are produced by interaction between the transmitted optical pulses and the atmospheric propagation channel. In some embodiments, the optical receiver subsystem includes a plurality of optical receive channels and receive optical components configured to direct the incoming detected optical signals to separate optical receive channels, depending on wavelength, polarization, or possibly other discriminating characteristics.

In some embodiments, each of the optical receive channels comprise an optical detector. The output of each optical detector is the respective output of the optical receive channel. In some embodiments, one or more of the optical detectors may be tuned to a specific wavelength. As an example, such wavelength may be, but is not required to be, the same as one of the transmitted wavelengths since Raman scattering re-emits at different wavelengths/frequencies based upon the molecular properties of the emitter. In some embodiments, one or more of the optical detectors may be tuned to a specific polarization, such as linear or circular. As an example, such polarization may be, but is not required to be, the same polarization as that of the transmitted optical signal. Polarization discrimination helps to analyze depolarization effects for aerosol microphysical properties retrieval.

In some embodiments, the optical detectors are high-resolution, high-speed, range-gating detectors. As an example, the optical detectors are range gating intensified charge coupled device (ICCD) cameras having a gating shutter of about 1 ns. In some embodiments, the optical detectors include components that can detect Doppler, fluorescence, and/or phosphorescence returns. In some embodiments, one or more of the imaging optical detectors may be replaced with photo sensor units or thermal sensors. In some embodiments, one or more of the optical detectors may use a 3D focal plane array as used in 3D Flash LADAR devices.

Figure 3:
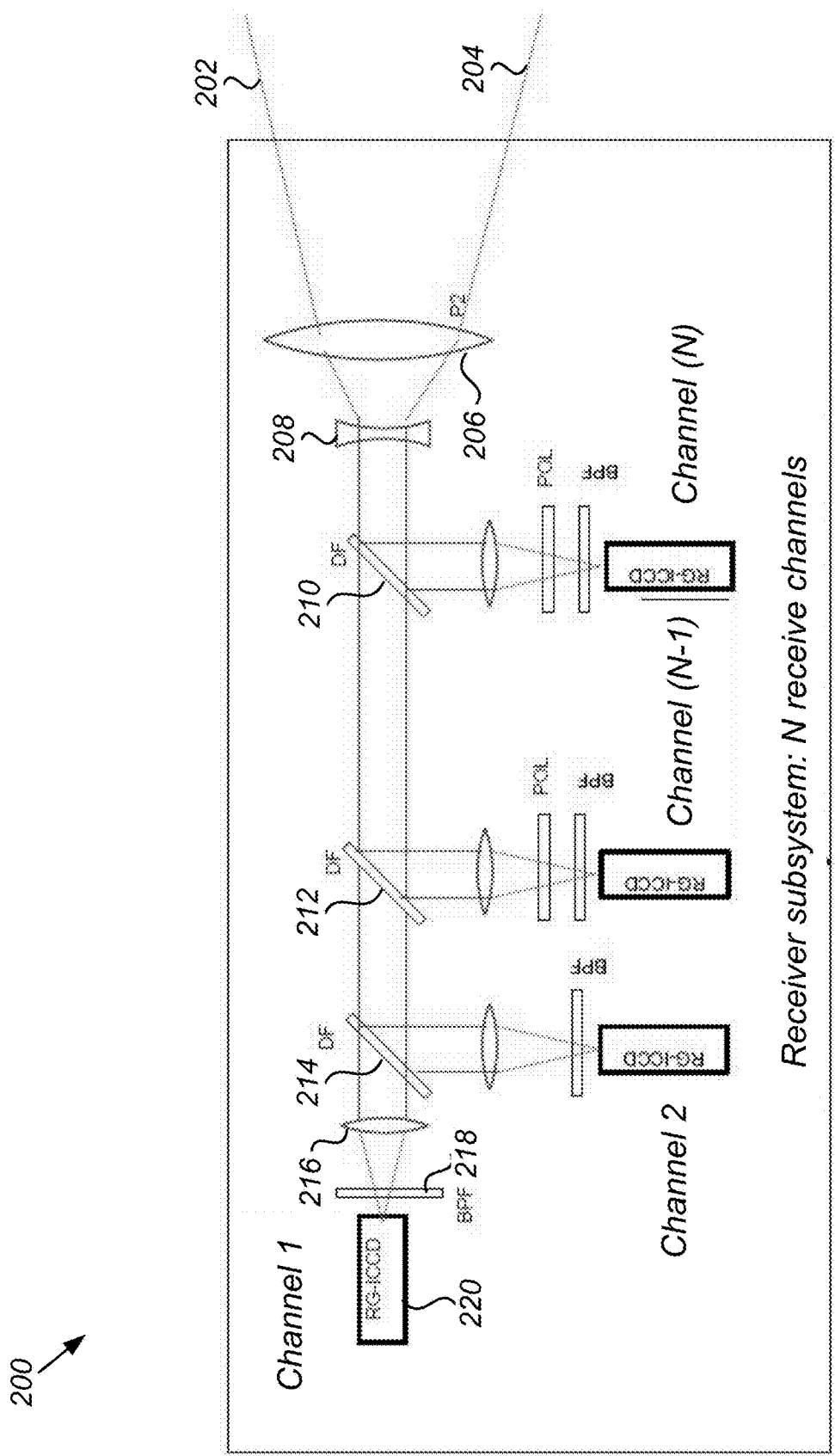
FIG. 3 shows a block diagram of an embodiment of a receiver sub-system in accordance with the Atmospheric Channel Characterization System and Method Using Target Image Information.

FIG. 3 shows a block diagram of an embodiment of a receiver subsystem 200 that may be used, for example, within system 10 and may serve as receiver subsystem 60. As shown, signals within a FOV defined by lines 202 and 204 from the atmospheric propagation channel are received by subsystem 200 by a standard collimating multi-lens system comprised of lens 206 and lens 208. The signals are then separated at various frequencies of interest (e.g. excitation wavelengths, inelastic Raman/fluorescence) into separate channels 1 to N via various narrow bandpass filters and dichromatic filters.

As shown, filter 210 directs some signals to channel N, filter 212 directs some signals to channel (N-1), filter 214 directs some signals to channel 2, and filter 214 directs some signals to channel 1. Each channel may include a lens 216 which directs received signals to a bandpass filter 218, which directs the signals to an imaging detector device 220. As an example, detector device 220 is a commercially available range-gating ICCD. However, other types of commercially-available optical detectors may be used, as discussed above.

Storage device 70 is operatively connected to receiver subsystem 60 and configured to store the output of the plurality of optical receive channels. Storage device 70 may comprise any device capable of storing data, signals, information, or the like. As an example, storage device 70 may be an optical disk or magnetic disk device. However, other storage devices may be used to suit particular applications or to achieve particular purposes, as would be recognized by one having ordinary skill in the art.

Figure 4:
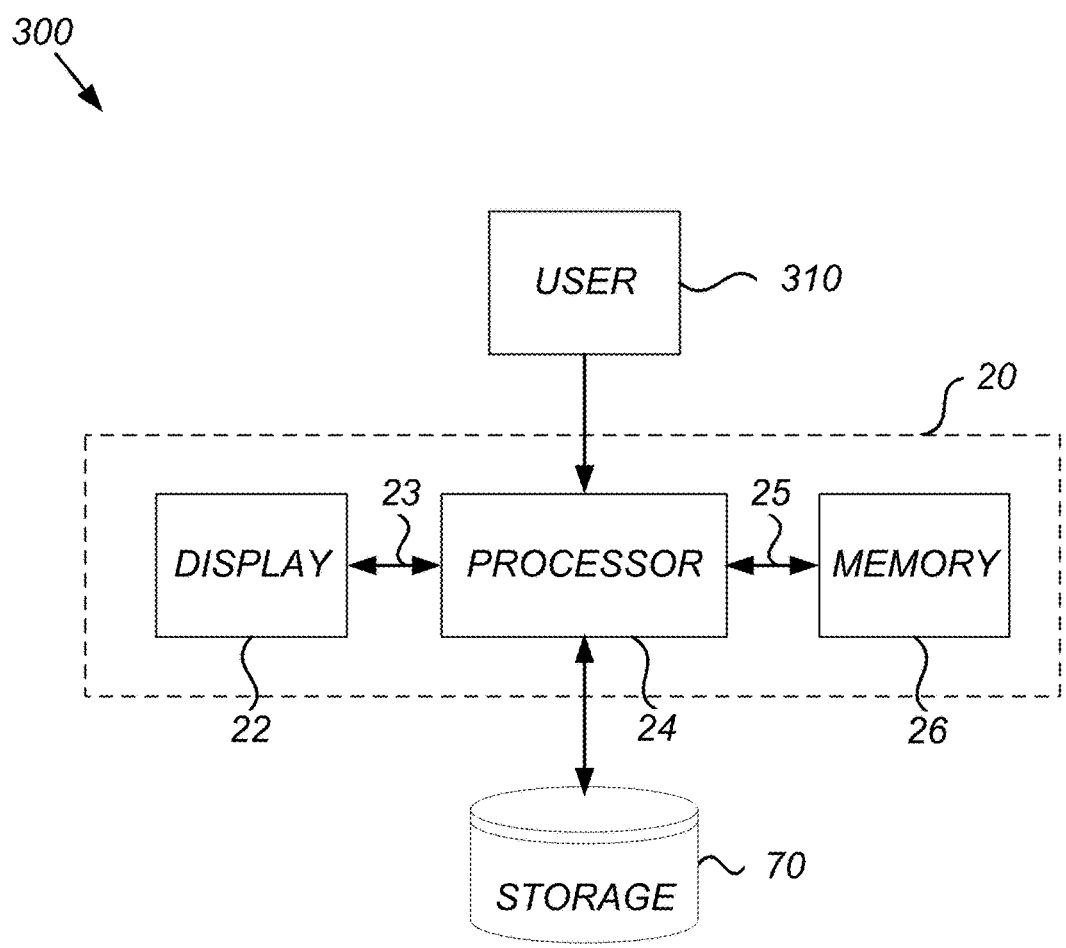
FIG. 4 shows a block diagram of an embodiment of a processing system in accordance with the Atmospheric Channel Characterization System and Method Using Target Image Information.

CPU 20 is operatively connected to storage device 70 and is configured to retrieve the stored output of the plurality of optical receive channels from the storage device and determine estimates of one or more parameters of the atmospheric propagation channel using the retrieved output. FIG. 4 shows a block diagram 300 of an embodiment of a CPU 20 that may be used in a system in accordance with a system in accordance with the disclosed embodiments, such as system 10 shown and described herein. As shown, CPU 20 is configured as a computer that may include a display 22, a processor 24 and a memory module 26. Display 22 and processor 24 may communicate via connection 23. Processor 24 and memory 26 may communicate via connection 25. Connections 23 and 25 may be wired or wireless.

Display 22 may comprise any type of display as recognized by one having ordinary skill in the art. For example, display 22 may be a liquid crystal display or a plasma display. Display 22 may be configured to display data, images, or other information to a user 310. In some embodiments, processor 24 may comprise any type of processing unit as recognized by one having ordinary skill in the art. Processor 24 may retrieve program instructions from memory module 26 to perform steps of the embodiments of the method described herein.

Memory 26 may comprise any type of volatile or non-volatile memory chip as recognized by one having ordinary skill in the art. For example, memory 26 may be flash memory, ROM, EPROM, EEPROM, RAM, DRAM, SRAM, or SDRAM. Memory 26 may contain program instructions stored therein. The program instructions may be executable by processor 24 to perform the embodiments of the methods, such as method 500, described herein. In some embodiments, processor 24 and memory 26 reside within the same chip.

A user 310 may interact with CPU 20 via display 22 and processor 24. As an example, user 310 may input information into CPU 20 via a keyboard, mouse, or other input device, as well as view pre-processed and processed data, images, or other information displayed on display 22. Storage device 60 is provided and coupled to processor 24 for storing information, instructions, etc. that may be used by processor 24.

In some embodiments, processor 24 or CPU 20 is further configured with the appropriate circuitry and/or software to determine the estimates of one or more physical parameters of the atmospheric propagation channel using one or more machine learning algorithms. The machine learning algorithms may, for example, be specially-trained and optimized for analyzing atmospheric propagation returns from aerosol, molecular scatter, optical turbulence, and refractivity, Raman scatter, fluorescence, and phosphorescence returns. In some embodiments, CPU 20 may further be configured with the appropriate circuitry and/or software to perform all of the data processing and analysis tasks as discussed herein. In some embodiments, the algorithms disclosed herein may be implemented on dedicated hardware such as an FPGA or embedded DSPs for maximum performance.

In some embodiments, processor 24 or CPU 20 is further configured to use the machine learning algorithms on the information contained within the image of target 50 to perform pattern-recognition and classification of target 50 based upon the one or more physical parameters of atmospheric propagation channel 40. As an example, such physical parameters of the atmospheric propagation channel may include aerosol, molecular scatter, optical turbulence, and refractivity, Raman scatter, fluorescence, and phosphorescence.

Figure 5:
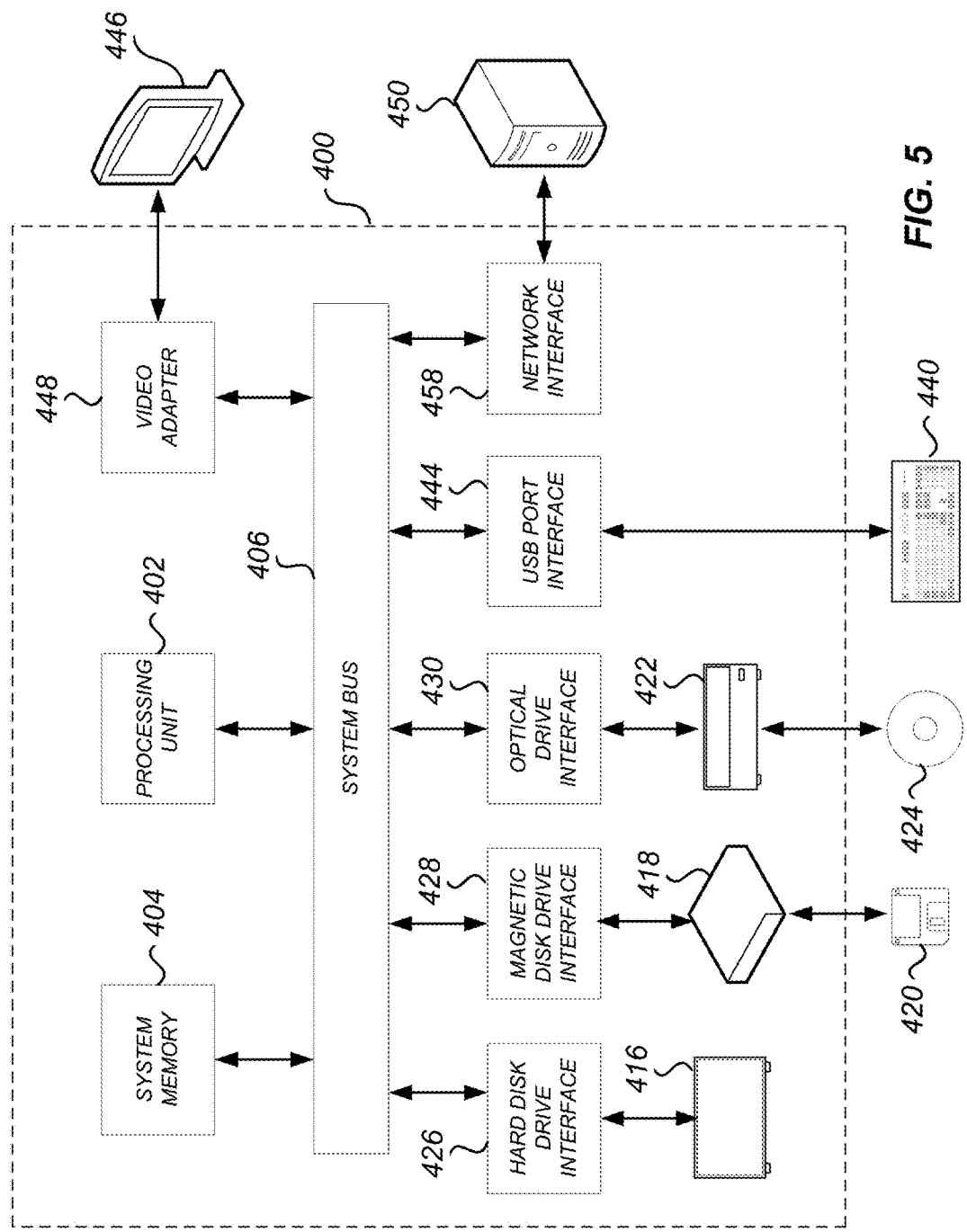
FIG. 5 shows a block diagram of another embodiment of a processing system in accordance with the Atmospheric Channel Characterization System and Method Using Target Image Information.

FIG. 5 shows a block diagram of another embodiment of a processing system in accordance with the Atmospheric Channel Characterization System and Method Using Target Image Information. FIG. 5 and the following description are intended to provide a brief, general description of a suitable computing environment in which the embodiments of the disclosed embodiments may be implemented. The embodiments will be described in the general context of computer-executable instructions, such as program modules, being executed by a computer.

Generally, program modules include routines, programs, objects, components, information structures, etc. . . . , that perform particular tasks or implements particular abstract information types. Moreover, those skilled in the art will appreciate that embodiments of the method disclosed herein may be practiced with other computer system configurations, including hand-held devices, multiprocessor systems, microprocessor-based or programmable consumer electronics, network personal computers, minicomputers, mainframe computers, and the like. Embodiments of the method may also be practiced in distributed computing environments where tasks are performed by remote processing devices that are linked through a communications network. In a distributed computing environment, program modules may be located on both local and remote memory storage devices.

In some embodiments, system 400 includes processing unit 402, system memory 404 and system bus 406 that operatively couple various system components to other system components (e.g., system bus 406 operatively couples system memory 404 to processing unit 402). Examples of system bus 406 include a memory bus, memory bus controller, peripheral bus and local bus using any of a variety of known bus structures. System memory 404 may include RAM, ROM, and basic input/output system. In some embodiments, system 400 comprises a specialized computing device specifically configured to run the embodiments of the method disclosed herein. In other embodiments, system 400 comprises a general purpose computing device, such as a personal computer.

System 400 further includes hard disk drive 416 for reading from and writing to a hard disk (not shown in FIG. 8) a magnetic disk drive 418 for reading from or writing to a removable magnetic disk 420 (e.g., 4.5-inch disk), and an optical disk drive 422 for reading from and writing to a removable optical disk 424 (e.g., CD-ROM and DVD). Hard disk drive 416, magnetic disk drive 418 and optical disk drive 422 are operatively connected to system bus 406 via hard disk drive interface 426, magnetic disk drive interface 428 and optical drive interface 430, respectively. The drives and their associated computer-readable media provide non-volatile storage of computer readable instructions, information structures, program modules and other information for personal computer 400.

The method steps of embodiments of the present method may be stored on a hard disk, magnetic disk 420 and optical disk 424. Although the exemplary environment described herein employs a hard disk, magnetic disk 420 and optical disk 424, it should be appreciated by those skilled in the art that other types of computer readable media that may store information accessible by a computer, (e.g., magnetic cassettes, flash memory cards, digital video disks, Bernoulli cartridges, random access memories and read only memories) may also be used in the exemplary operating environment without departing from the scope or spirit of embodiments of the method.

Figure 6:
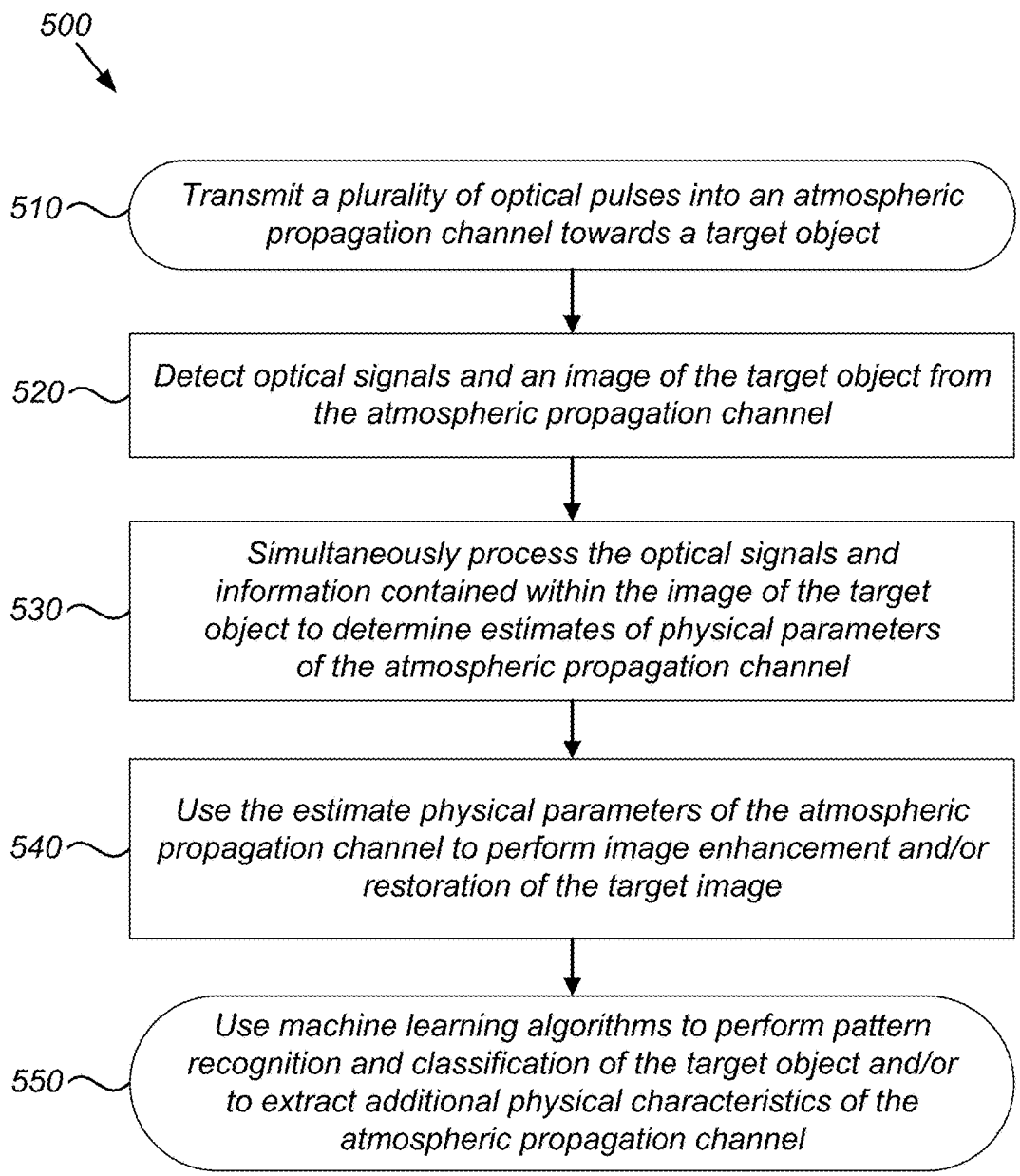
FIG. 6 shows a flowchart of an embodiment of a method in accordance with the Atmospheric Channel Characterization System and Method Using Target Image Information.

A user may enter commands and information into system 400 via input devices such as keyboard 440 and pointing devices (e.g., mouse) (not shown in FIG. 6). Examples of input devices (not shown in FIG. 6) include a microphone, joystick, game pad, and satellite dish. Input devices may be operatively connected to processing unit 402 via universal serial bus (USB) port interface 444 that is operatively connected to system bus 406. Input devices may also be operatively connected to processing unit 402 via other interfaces (e.g., parallel port, serial port and game port) that are operatively connected to system bus 406. Monitor 446 is operatively connected to system bus 406 via video adapter 448. Other peripheral devices (e.g., speakers and printers) may be operatively connected to system 400 via other interfaces. System 400 may operate in a networked environment using logical connections to one or more remote computers such as remote computer 450 via network a network, such as a local area network, wide area network, and wireless network. Examples of remote computer 450 include a personal computer, server, router, network personal computer, peer device and network node.

FIG. 6 shows a flowchart of an embodiment of a method in accordance with the Atmospheric Channel Characterization System and Method Using Target Image Information. As an example, method 500 may be performed by system 10 as shown in FIG. 1, incorporating subsystems 100 and 200 as shown in FIGS. 2 and 3, respectively, and will be discussed with reference thereto. Also, while FIG. 6 shows one embodiment of method 500 to include steps 510-550, other embodiments of method 500 may contain fewer or more steps. Further, while in some embodiments the steps of method 500 may be performed as shown in FIG. 5, in other embodiments the steps may be performed in a different order, or certain steps may occur simultaneously with one or more other steps.

Method 500 may begin with step 510, which involves transmitting, using an optical device 102, a plurality of optical pulses 32 into an atmospheric propagation channel 40 towards a target object 50. Method 500 may then proceed to step 520, which involves detecting, using an imaging device 220, more than one optical signals 52 and an image, also contained within signals 52, of target object 50 from the atmospheric propagation channel 40.

In some embodiments of method 500, prior to step 530, method 500 includes the steps of storing the output of the imaging device 220 in a storage device 70 operatively connected to imaging device 220 and retrieving the stored output of imaging device 220 from storage device 70. These steps allow for making estimate determinations at a separate point in time than the information collection is performed.

Method 500 may then proceed to step 530, which involves simultaneously processing, using a processor 20 (or 24) operatively connected to the imaging device 220, the optical return signals from the propagation channel, which may include but are not limited to the elastic backscatter return signals, inelastic backscatter return signals, polarization signals and information contained within the image of the target object—such as point, line, and edge blur and deformations, image spatial-spectral frequency response content, contrast, inter-frame temporal characteristics, target and clutter range and material properties—to determine estimates of one or more physical parameters of atmospheric propagation channel 40.

In some embodiments, the step of determining estimates of one or more physical parameters of the atmospheric propagation channel is performed using one or more machine learning algorithms specifically configured to analyze hyperspectral atmospheric propagation returns. As an example, the machine learning algorithms may include a semi-supervised learning machine learning algorithm, a support vector machine learning algorithm, or an artificial neural network algorithm. In some embodiments, the machine learning algorithm is used to select one or more optimal weighting coefficients for a superposition of weak-learner general no-reference image quality metrics, which serve as input features to the machine learning algorithm, possibly along with the raw image pixel data or segmented regions of the image data which have been extracted based on image analysis identifying important sub-regions of the image.

In some embodiments, method 500 may further comprise step 540, which involves using the estimated physical parameters of the atmospheric propagation channel to perform image enhancement and/or restoration of the target image. As an example, step 540 may be performed by blind image deconvolution and restoration using an inverse Wiener filter estimated using the extracted channel parameters. Step 540 may help to improve the performance of the pattern recognition and/or classification tasks, or other relevant tasks such as target acquisition or tracking.

In some embodiments, method 500 includes step 550, which involves using the machine learning algorithms on the information contained within the image of target 50 to perform pattern-recognition and classification of the target object and/or to extract additional atmospheric propagation channel 40 physical characteristics to supplement the range-gated returns. In embodiments of method 500 including step 540, method 550 may involve pattern-recognition and classification of the target object using the enhanced or restored version of the target performed in step 540.

Based on initial training of the machine learning algorithms with carefully constructed sets of representative imagery taken from both real-world field measurements and controlled computer modeling & simulations under a variety of known atmospheric conditions, the algorithm learns to associate specific n-tuples of atmospheric parameter values with target image characteristics, such as blur, contrast variations, linear deformations, anisotropy, entropy, energy distribution.

In some embodiments, step 550 is performed using one or more image quality metric algorithms. In some embodiments, step 550 is performed using one or more image-restoration/deconvolution algorithms. As an example, details about the use of a deconvolution algorithm is found in U.S. Pat. No. 9,129,369, entitled "Method for Characterizing an Atmospheric Channel", to Wayne et al.

Some embodiments involve a unique application of extensive and specialized domain expertise to define an algorithm applying machine learning methods to extract atmospheric parameters from passive imagery. The performance of a machine learning-based atmospheric parameter extraction algorithm may be dependent on the steps of feature-definition and generation/selection of the machine learning training data sets. These steps involve extensive and specialized domain knowledge in the complex fields of atmospheric aerosol physics, electromagnetic wave propagation in random media, atmospheric turbulence and fluid dynamics, as well as optics, image processing, and image quality metrics & analysis.

In some embodiments, method 500 further includes the step of performing the atmospheric channel parameter retrieval inversion computations, using both the plurality of range-gated optical returns as well as the image of the remote target-of-opportunity, to create estimates of the atmospheric parameters of interest characterizing the atmospheric propagation channel conditions. A person having ordinary skill in the art will recognize that the topic of parameter retrieval through inverse solution methods is an open and active area of academic and scientific research and that several existing methods could be incorporated into the embodiments disclosed herein.

As an example, the parameters of interest characterizing the propagation may include one or more of the following: atmospheric absorption, scattering, transmission, and extinction coefficients, particle microphysical properties (e.g. complex refractive indices of various detected aerosols, aerosol size/mass/volume distributions, aerosol size distribution function), atmospheric water vapor content, air temperature, wind velocity, cloud parameters (e.g. liquid water content, droplet size, # density, and optical depth), and optical turbulence parameters (e.g. refractive index structure parameter, Fried atmospheric coherence radius, isoplanatic angle, inner scale of turbulence, outer scale of turbulence, Greenwood frequency). It should be recognized by a person having ordinary skill in the art that other parameters of interest may be estimated and still fall within the scope of the embodiments disclosed herein.

Method 500 may be stored on a computer readable storage medium, the methods represented by computer readable programming code. Method 500 may be implemented using a programmable device, such as a computer-based system. Method 500 may be implemented using various programming languages, such as "C" or "C++".

Various computer-readable storage mediums, such as magnetic computer disks, optical computer disks, electronic memories and the like, may be prepared that may contain program instructions that direct a device, such as a computer-based system, to implement the steps of method 500. Once an appropriate device has access to the program instructions contained on the computer-readable storage medium, the storage medium may provide the information and programs to the device, enabling the device to perform method 500.

For example, if a computer disk containing appropriate materials, such as a source file, an object file, or an executable file is provided to a computer, the computer receives the information, configures itself, and perform the steps of method 500. The computer would receive various portions of information from the disk relating to different steps of method 500, implement the individual steps, and coordinate the functions of the individual steps.

Many modifications and variations of the embodiments disclosed herein are possible in light of the above description. Within the scope of the appended claims, the disclosed embodiments may be practiced otherwise than as specifically described. Further, the scope of the claims is not limited to the implementations and embodiments disclosed herein, but extends to other implementations and embodiments as may be contemplated by those having ordinary skill in the art.

I claim:
1. A system comprising:
an optical transmitter subsystem configured to transmit a plurality of hyperspectral optical pulses into an atmospheric propagation channel, the optical transmitter subsystem comprising a plurality of optical transmit channels each tuned to a separate wavelength and transmit optical components configured to combine the output of the optical transmit channels to produce the plurality of hyperspectral optical pulses;
an optical receiver subsystem configured to detect optical signals from the atmospheric propagation channel, the optical signals produced by interaction between the transmitted hyperspectral optical pulses and the atmospheric propagation channel, the optical receiver subsystem comprising a plurality of optical receive channels and receive optical components configured to direct the detected optical signals to separate optical receive channels, depending on at least one of wavelength and polarization;
a storage device, operatively connected to the optical receiver subsystem, configured to store the output of the plurality of optical receive channels; and
a processor, operatively connected to the storage device, configured to retrieve the stored output of the plurality of optical receive channels from the storage device and determine estimates of the optical turbulence parameter of the atmospheric propagation channel using the retrieved output, wherein the processor is further configured to use the estimates of the optical turbulence parameter of the atmospheric propagation channel to perform blind image deconvolution and restoration using an inverse Werner filter of a target image obtained from a target within the atmospheric propagation channel.

2. A system comprising:
an optical transmitter subsystem configured to transmit a plurality of hyperspectral optical pulses into an atmospheric propagation channel, the optical transmitter subsystem comprising a plurality of optical transmit channels each tuned to a separate wavelength and transmit optical components configured to combine the output of the optical transmit channels to produce the plurality of hyperspectral optical pulses;
an optical receiver subsystem configured to detect optical signals from the atmospheric propagation channel, the optical signals produced by interaction between the transmitted hyperspectral optical pulses and the atmospheric propagation channel, the optical receiver subsystem comprising a plurality of optical receive channels and receive optical components configured to direct the detected optical signals to separate optical receive channels, depending on at least one of wavelength and polarization;
a storage device, operatively connected to the optical receiver subsystem, configured to store the output of the plurality of optical receive channels; and
a processor, operatively connected to the storage device, configured to retrieve the stored output of the plurality of optical receive channels from the storage device and determine estimates of the optical turbulence parameter of the atmospheric propagation channel using the retrieved output, wherein the processor is further configured to use the estimates of the optical turbulence parameter of the atmospheric propagation channel to perform blind image deconvolution and restoration using an inverse Werner filter of a target image obtained from a target within the atmospheric propagation channel, wherein the processor is further configured to use the machine learning algorithms on information contained within the target image to perform pattern-recognition and classification of the target based upon the optical turbulence parameter of the atmospheric propagation channel.

* * * * *